(12) United States Patent
Fiedorowicz

(10) Patent No.: US 9,746,357 B2
(45) Date of Patent: Aug. 29, 2017

(54) FLOW SENSING METER

(71) Applicant: OES MEDICAL LIMITED, Witney (GB)

(72) Inventor: Richard Fiedorowicz, Abingdon (GB)

(73) Assignee: OES MEDICAL LIMITED, Witney, Oxfordshire (GB)

( * ) Notice: Subject to any disclaimer, the term of this patent is extended or adjusted under 35 U.S.C. 154(b) by 14 days.

(21) Appl. No.: 14/695,162

(22) Filed: Apr. 24, 2015

(65) Prior Publication Data

US 2016/0313152 A1  Oct. 27, 2016

(51) Int. Cl.
| | |
|---|---|
| G01F 1/40 | (2006.01) |
| A61M 16/10 | (2006.01) |
| A61M 16/01 | (2006.01) |
| A61M 16/00 | (2006.01) |

(52) U.S. Cl.
CPC ............... *G01F 1/40* (2013.01); *A61M 16/01* (2013.01); *A61M 16/104* (2013.01); *A61M 2016/0027* (2013.01); *A61M 2016/0036* (2013.01); *A61M 2202/0241* (2013.01); *A61M 2205/3334* (2013.01)

(58) Field of Classification Search
CPC ............... G01F 1/40; A61M 16/0003; A61M 2205/3334; A61M 2202/0241; A61M 2016/003; A61M 16/104
See application file for complete search history.

(56) References Cited

U.S. PATENT DOCUMENTS

| | | | | |
|---|---|---|---|---|
| 3,677,300 A | * | 7/1972 | King | F01N 1/082 137/625.3 |
| 3,698,474 A | * | 10/1972 | Rowley | E21B 33/068 137/1 |
| 3,838,598 A | * | 10/1974 | Tompkins | G01F 1/42 73/861.52 |
| 4,088,155 A | * | 5/1978 | Echtler | B01J 8/008 138/40 |
| 4,118,973 A | * | 10/1978 | Tucker | G01N 11/08 73/54.04 |

(Continued)

FOREIGN PATENT DOCUMENTS

| | | |
|---|---|---|
| EP | 1046887 A1 | 10/2000 |
| WO | 9920984 A1 | 4/1999 |

OTHER PUBLICATIONS

European Search Report for EP 14003998 dated Mar. 18, 2015.

*Primary Examiner* — David Bolduc
(74) *Attorney, Agent, or Firm* — Heslin Rothenberg Farley & Mesiti P.C.

(57) ABSTRACT

A fluid flow sensor includes a hollow cylindrical casing containing a large number of solid spheres of identical diameter, packed tightly together. Fluid inflow and fluid outflow blocks are mounted to opposite ends of the casing, forming a fluid-tight seal. The fluid inflow and outflow blocks each enclose a generally conical fluid chamber tapering from where it meets an end of an interior of the casing to a respective inlet passage or outlet passage. Circular grilles divide the casing from each fluid chamber and retain the spheres in place. A pressure differential across the casing is measured via side passages extending laterally from each fluid chamber. For a given fluid, a given casing diameter and a given sphere diameter, this pressure differential can be converted to a fluid flow rate.

19 Claims, 2 Drawing Sheets

(56) References Cited

U.S. PATENT DOCUMENTS

Figure 1:
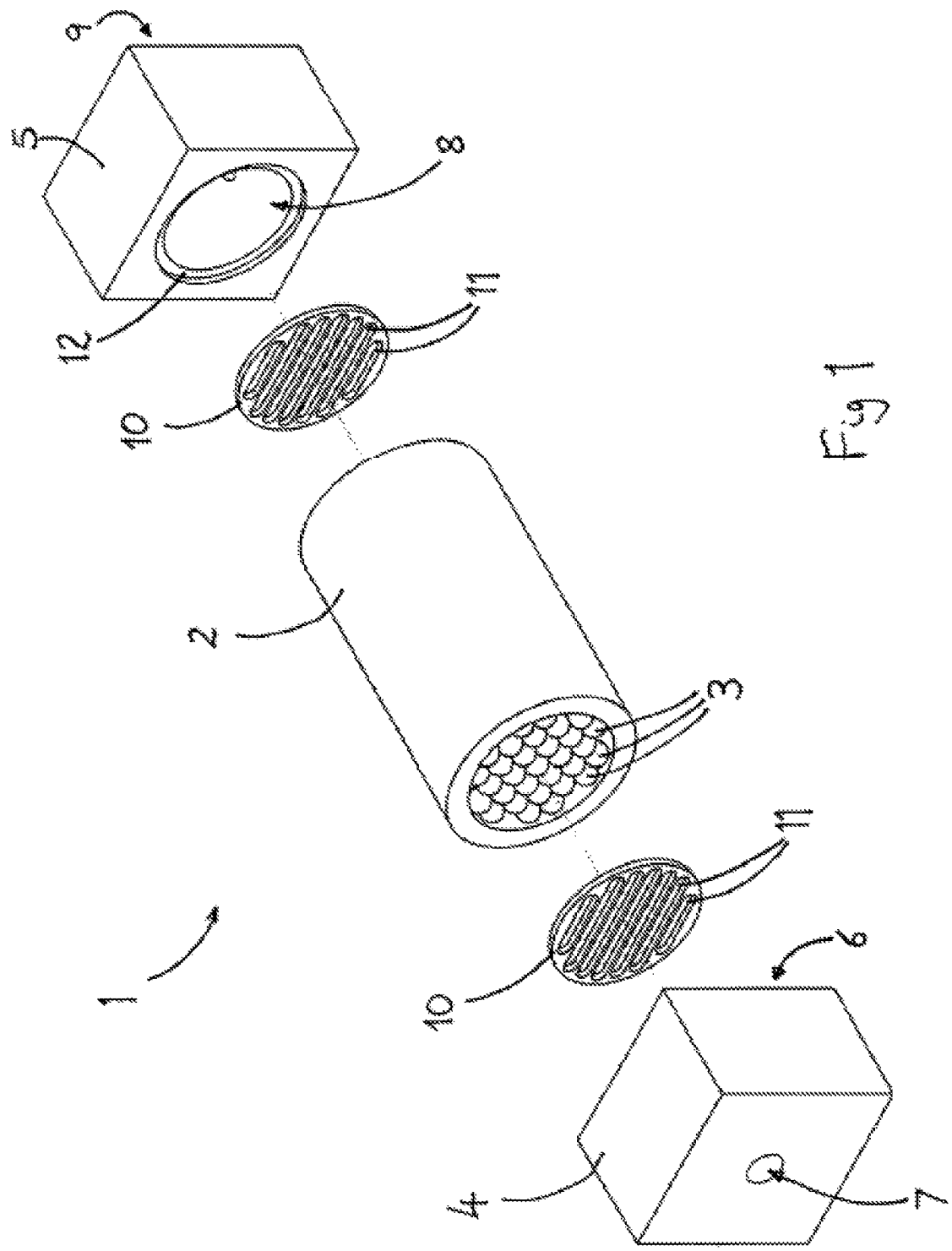

| | | | | |
|---|---|---|---|---|
| 4,315,431 A * | 2/1982 | Hawk | ................ | G01F 5/00 |
| | | | | 138/43 |
| 4,524,616 A * | 6/1985 | Drexel | ................ | G01F 5/00 |
| | | | | 73/203 |
| 4,722,829 A * | 2/1988 | Giter | ................ | A61M 1/1698 |
| | | | | 128/DIG. 3 |
| 4,860,783 A * | 8/1989 | Megee | ................ | F16K 17/20 |
| | | | | 137/268 |
| 5,332,005 A | 7/1994 | Baan | | |
| 5,824,894 A * | 10/1998 | Lucas | ................ | G01F 1/6847 |
| | | | | 73/202.5 |
| 6,579,041 B2 * | 6/2003 | Hobbs | ................ | B07B 7/06 |
| | | | | 138/42 |
| 6,601,460 B1 | 8/2003 | Materna | | |
| 7,992,454 B2 * | 8/2011 | Purdy | ................ | G01F 1/48 |
| | | | | 73/861.52 |
| 2002/0103444 A1 * | 8/2002 | Ricciardelli | ................ | A61B 5/087 |
| | | | | 600/532 |
| 2006/0101908 A1 * | 5/2006 | Meneghini | ................ | G01F 5/00 |
| | | | | 73/202.5 |
| 2008/0250854 A1 * | 10/2008 | Ding | ................ | G01F 1/48 |
| | | | | 73/198 |
| 2014/0163693 A1 * | 6/2014 | McKnight | ................ | A61F 2/04 |
| | | | | 623/23.68 |

\* cited by examiner

FLOW SENSING METER

BACKGROUND OF THE INVENTION

The present invention relates to the field of devices for determining fluid flow rates. More particularly, but not exclusively, it relates to a device for determining flow rates of gases in anesthetic ventilators.

Many forms of equipment require a flow rate of liquids, gases or vapors through the equipment to be measured, whether purely for recording purposes or so that deviations from a desired fluid flow rate may be identified and corrected. A wide range of flow rate measuring devices are known, but many are suitable only for a limited range of fluid viscosities and cannot easily be adjusted for use with fluids having viscosities outside this range.

For example, in the field of anesthetic ventilators, a general idea of flow rates can be obtained by passing a carrier gas or vapor flow through a restricted orifice and determining a pressure drop across the orifice. However, this approach has been found to be insufficiently reliable. For example, the exact configuration and size of the orifice can be critical, leading to poor reproductibility between different units of apparently identical design. A particular orifice size is only effective for a particular, usually narrow, range of fluid viscosities. Additionally, flow through such an orifice can become non-linear or even turbulent at high fluid flow rates, and a restricted orifice may also significantly restrict the fluid flow rates that it is intended to measure.

Similar issues are believed to apply to other fluid flow measuring devices in a range of different fields, working with a range of different fluids.

It is hence an object of the present invention to provide a fluid flow sensing and measuring device that has greater flexibility and adaptability than existing devices, and which obviates some or all of the above drawbacks of existing devices.

BRIEF SUMMARY OF THE INVENTION

According to a first aspect of the present invention, there is provided a fluid flow sensing device comprising a chamber extending from a first opening at a first end of the chamber to a second opening at a second end of the chamber remote from the first end, a plurality of substantially identical bodies so packed into said chamber as to define a plurality of indirect fluid passages extending between said first and second openings, means to direct a flow of fluid to be measured through the chamber and means to determine a differential pressure between fluid adjacent the first end of the chamber and fluid adjacent the second end of the chamber.

Preferably, the flow sensing device comprises means to calculate a fluid flow rate from said differential pressure.

Alternatively, the fluid flow rate may be determined by an operator of the device, optionally using predetermined graphs, tables or other conversion means between differential pressure and fluid flow rate.

Preferably, the chamber has a substantially constant cross-section between said first and second ends.

In a preferred embodiment, the chamber comprises an elongate hollow cylindrical vessel, said first and second openings being located at longitudinally remote ends of the vessel.

Said first and second openings may then each comprise a respective open end of said vessel.

Preferably, each of said plurality of substantially identical bodies comprises a solid body.

Advantageously, each of said plurality of substantially identical bodies is substantially spherical.

Each said substantially spherical body may have the same preselected body diameter.

Preferably, said plurality of substantially identical bodies substantially fills an interior of the chamber.

Said substantially identical bodies may be substantially regularly packed within the chamber.

Alternatively, said substantially identical bodies may be substantially randomly packed within the chamber.

The substantially identical bodies may be so packed as to provide a close packing arrangement with minimal unoccupied space within the chamber, such as one of a random close packed arrangement, a cubic close packed arrangement or a hexagonal close packed arrangement.

Preferably, the means to direct a flow of fluid through the chamber means comprises a fluid inlet operatively connected to the first opening and a fluid outlet operatively connected to the second opening.

Each of said fluid inlet and outlet may comprise a plenum chamber, contiguous at one end with a respective opening of the chamber.

Preferably, said means to determine a differential pressure is operatively connected between said fluid inlet and said fluid outlet.

Advantageously, said means to determine a differential pressure is operatively connected between said plenum chambers through a respective aperture extending through a respective wall of each said plenum chamber.

Preferably, said first and second openings of the chamber are each provided with means to retain the plurality of substantially identical bodies within the chamber.

Each means to retain the plurality of substantially identical bodies within the chamber may comprise a grille having a grille aperture size below a minimum dimension of each substantially identical body.

Said grille may comprise at least one grille aperture having a profile differing substantially from a cross-sectional profile of each said substantially identical body, so as to avoid said grille aperture being blocked by a body in contact with the grille.

Preferably, an average diameter of each said substantially identical body is between one third and one twentieth of a chamber diameter of the chamber, said chamber diameter being taken orthogonal to an axis extending between its respective first and second openings.

Advantageously, said average diameter of the substantially identical bodies is less than one quarter of said chamber diameter.

Said average diameter of the substantially identical bodies may be at least one tenth of said chamber diameter.

Optionally, said average diameter of the substantially identical bodies may be less than one fifth of said chamber diameter.

Optionally, said average diameter of the substantially identical bodies may be at least one eighth of said chamber diameter.

In a preferred embodiment, the fluid flow sensing device is so configured that said plurality of substantially identical bodies may be removed and replaced with a second plurality of alternative substantially identical bodies, said alternative substantially identical bodies for example having a different diameter.

The chamber may then be provided with means to retain the plurality of substantially identical bodies within the chamber that are selectably removable.

The fluid inlet and/or outlet may then be selectably detachable from the chamber, so as to allow access to a respective opening.

Preferably, the fluid flow sensing device comprises a gas flow sensing device; i.e. said fluid comprises a gas.

According to a second aspect of the present invention, there is provided anesthetic ventilator apparatus, provided with fluid flow sensing device as described in the first aspect above.

BRIEF DESCRIPTION OF THE DRAWING FIGURES

Figure 2:
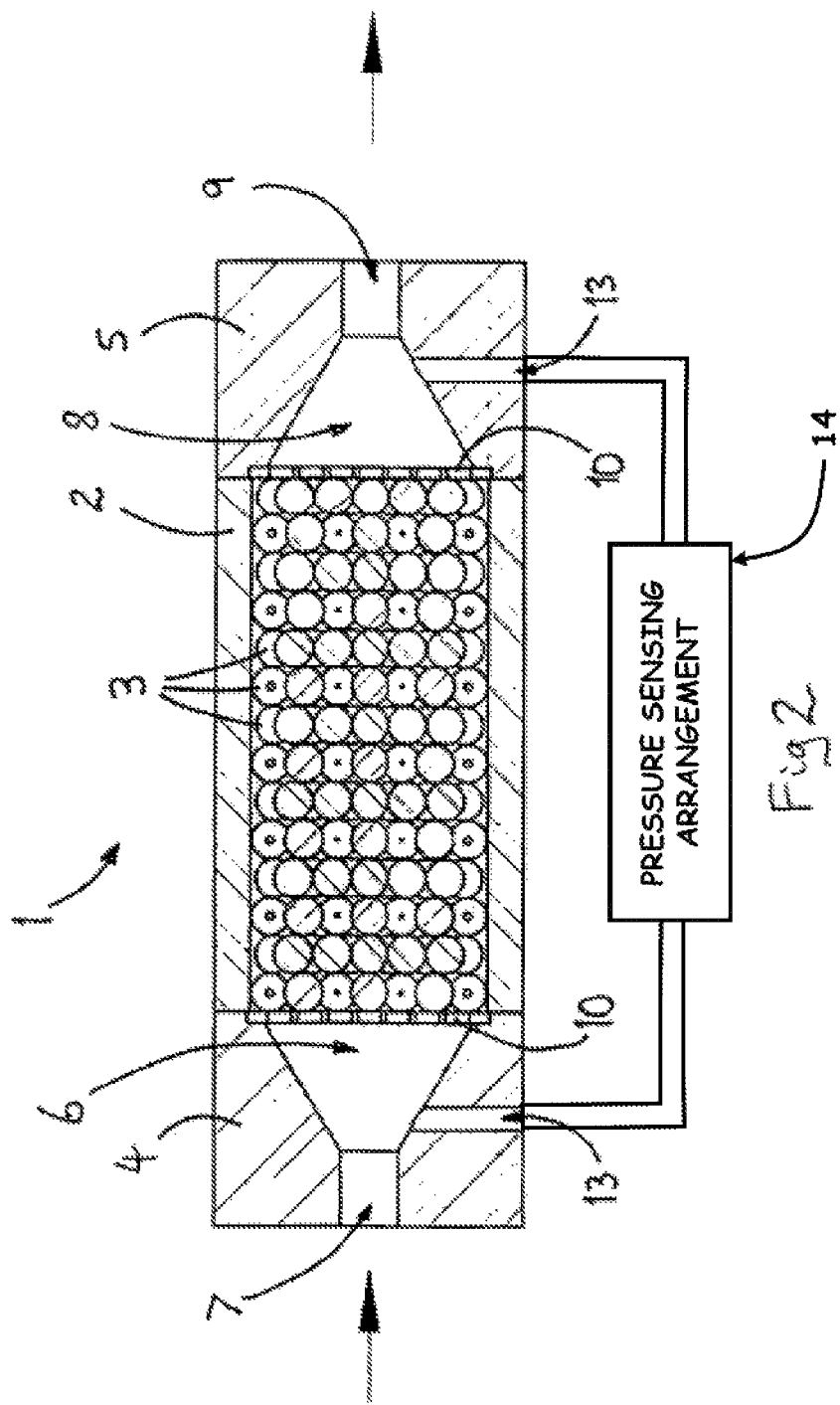

An example of the present invention will now be more particularly described, by way of example and with reference to the Figures of the accompanying drawings, in which FIG. 1 is an exploded isometric view of a fluid flow sensor embodying the present invention; and FIG. 2 is a longitudinal cross-sectional view of the fluid flow sensor of FIG. 1.

DETAILED DESCRIPTION

Referring now to the Figures, and to FIG. 1 in particular, a fluid flow sensor 1 embodying the present invention comprises a hollow metal cylindrical casing 2 filled with a plurality of solid metal balls 3, each of identical diameter. Ideally, the balls 3 are of stainless steel. (Alternative fluid flow casings and ball packings may be made of non-metallic materials, such as plastics materials, particularly thermosetting resins, or ceramics materials, depending on compatibility with the fluids in question, strength requirements, operating temperatures, and other criteria known routinely to the skilled person; an important criterion that may also need to be taken into account when using alternative materials is to avoid porosity and to avoid materials that might selectively absorb or adsorb a component of the fluids in question—e.g. when measuring a moisture-laden vapor, the fluid flow sensor should not also act as a desiccator).

In this embodiment, the balls 3 are shown packed in a regular, layered array (see also FIG. 2). However, it had been found that a more important consideration is that the balls 3 should be packed tightly and that the cylindrical casing 2 is filled with as many balls as possible. A perfectly regular geometrical array is not essential, and random or pseudo-random close packing appears to be sufficient.

The cylindrical casing 2 may thus conveniently be filled as follows. Balls 3 are poured into the casing 2 until it appears full, and the casing 2 is then tapped to settle the packing of the balls 3. The resulting free volume released within the casing 2 is then topped-up with a few further balls 3, filling the casing 2 to a maximum practical extent.

In the illustrated embodiment, the diameter of each ball 3 is between one-sixth and one-seventh of an internal diameter of the cylindrical casing 2. Larger or smaller balls 3 may be used, with effects on the performance of the fluid flow sensor 1 as described below. However, as the diameter of the balls 3 becomes a larger proportion of the internal diameter of the cylindrical casing 2, producing a tight packing becomes increasingly difficult.

A fluid inflow block 4 is mounted to the first end of the cylindrical casing 2, and a fluid outflow block 5 is mounted to a second end of the cylindrical casing 2, remote from the first. Each of the fluid inflow block 4 and the fluid outflow block 5 makes a fluid-tight seal with the respective end of the cylindrical casing 2.

The fluid inflow block 4 contains a generally conical fluid chamber 6 (not visible in this view), diverging from a coaxial inlet passage 7 towards an open mouth of the chamber 6. Said open mouth corresponds substantially in diameter to the internal diameter of the cylindrical casing 2, with which it is coaxially aligned.

Similarly, the fluid outflow block 5 contains a generally conical fluid chamber 8 that converges from its open mouth towards a coaxial outflow passage 9 (not visible in this view). Said open mouth also corresponds substantially in diameter to the internal diameter of the cylindrical casing 2, and is aligned coaxially therewith. Fluid chambers 6 and 8 may have shapes other than generally conical.

The fluid inflow block 4 and the fluid outflow block 5 are each fitted with a circular grille 10, which has a plurality of elongate, narrow, parallel slots 11 extending through it, and is seated in an annular recess 12 extending around a rim of the open mouth of each respective fluid chamber 6, 8.

When the respective fluid inflow and outflow blocks 4, 5 are fitted to respective ends of the cylindrical casing 2, these grilles 10 thus prevent the balls 3 escaping from the cylindrical casing 2. The elongate slots 12 have this shape to avoid balls 3 blocking the slots 12, and so blinding the grille 10, as might occur with circular grille holes.

Referring now to FIG. 2, the packing of the balls 3 within the cylindrical casing 2 can more clearly be seen, as can the respective fluid chambers 6, 8 and inlet/outlet passages 7, 9 of the fluid inflow and outflow blocks 4, 5.

Fluid, such as air, a carrier gas, a vapor-laden carrier gas or even a liquid, may thus be passed into the fluid flow sensor 1, through the inlet passage 7 and the fluid chamber 6, along the cylindrical casing 2 between the balls 3, and out through the fluid chamber 8 and the outlet passage 9.

The fluid inflow block 4 and the fluid outflow block 5 each have a side passage 13 extending radially outwardly from the respective conical fluid chambers 6, 8. These side passages 13 are each operatively connected to a pressure sensor arrangement 14, such as a differential pressure transducer HDOM050DE8H—0 to 50 mBar, available from First Sensor (Sensortechnics) of Munich, Germany, which detects a differential pressure between the fluids in the respective fluid chambers 6, 8. This differential pressure is sufficiently close, for the purposes of the present invention, to a differential pressure across the cylindrical casing 2. The pressure sensing arrangement may comprise other known pressure measuring devices, such as a two single port pressure transducers used as a pair. A computer, calculator, comparator or the like may be included in, or linked to, the pressure sensing arrangement for determining fluid flow rate from the detected differential pressure in any known manner.

Due to the closely packed arrangement of the balls, there are no direct paths for fluid through the cylindrical casing 2 from end to end (i.e. unobstructed paths allowing flow in a straight line from the first end to the second end of the cylindrical casing). Because of the balls 3 packed into the cylindrical casing 2, there are, however, a large number of indirect paths around the balls that fluid may follow, the cross-sectional dimensions of these indirect paths being closely linked to the diameter of the balls 3. There will thus be a resistance to flow of the fluid, which depends on the dimensions of the indirect paths (and hence the diameters of the balls 3), on the viscosity of the fluid, and on the overall fluid flow rate. This resistance causes the differential pressure that can be measured across the cylindrical casing 2.

Since the ball 3 size will be constant, as will the fluid viscosity (as long as the local temperature remains reasonably constant), the differential pressure can be related directly to the flow rate of fluid through the fluid flow sensor 1.

It has been found that the fluid flow sensor 1 described can accommodate a wide range of flow rates without adjustment, since the flow of the fluid between the balls 3 remain laminar. A particular fluid flow sensor 1 can easily be modified to measure flow rates in a different range, and/or to measure flows of a fluid having a different viscosity, by removing a fluid inflow or outflow block 4, 5 and associated grille 10, removing the particular balls 3 in use, and replacing them with a packing of balls 3 having a different diameter.

After reassembly, the fluid flow sensor 1 may be used as described above, while substituting appropriate parameters such as ball diameter and fluid viscosity into the algorithm for conversion of differential pressure to fluid flow rate.

It is also envisaged that alternative embodiments with different cylindrical casing 2 diameters and/or lengths could be used. These will also operate over different fluid flow rate ranges, and can also be used with balls 3 having different absolute sizes and/or different sizes relative to the cylindrical casing 2.

The repeatability of results between different units has been found to be excellent.

The benefits of the fluid flow sensor 1 described have so far been found mainly in monitoring the flow of gases and vapors, for example in anesthetic ventilators and the like. However, there are indications that the same approach is equally suitable for liquids, only needing to allow for their higher viscosities.

The number of alternative paths through the cylindrical casing 2, around the balls 3, means that blockages are far less likely to occur than for existing systems using a single orifice. Also, the fluid flow sensor 1 of the present invention is far less likely to restrict the fluid flow that is being monitored, compared with the single narrow orifice of existing systems.

The invention claimed is:

1. A fluid flow sensing device, comprising:
   a chamber having a first end and a second end, said second end being remote from said first end, and said chamber extending between a first opening at said first end of the chamber and a second opening at said second end of the chamber;
   a plurality of substantially identical spherical bodies packed into said chamber, filling said chamber, and defining between said plurality of substantially identical spherical bodies a plurality of indirect fluid passages extending between said first opening and said second opening;
   means to direct a fluid flow to be measured through the chamber; and
   means to determine a differential pressure across at least a full length of the chamber from fluid adjacent the first end of the chamber and fluid adjacent the second end of the chamber.

2. The fluid flow sensing device as claimed in claim 1, further comprising means to calculate a fluid flow rate from said differential pressure.

3. The fluid flow sensing device as claimed in claim 1, wherein said chamber has a substantially constant cross-section between said first end and said second end.

4. The fluid flow sensing device as claimed in claim 1, wherein said chamber comprises an elongate hollow cylindrical vessel, said first end and said second end comprising longitudinally remote ends of the elongate hollow cylindrical vessel.

5. The fluid flow sensing device as claimed in claim 4, wherein said first opening and said second opening each comprise a respective open end of said elongate hollow cylindrical vessel.

6. The fluid flow sensing device as claimed in claim 1, wherein each of said plurality of substantially identical spherical bodies comprises a solid body.

7. The fluid flow sensing device as claimed in claim 1, wherein each of said plurality of substantially identical spherical bodies has an identical body diameter.

8. The fluid flow sensing device as claimed in claim 1, wherein said plurality of substantially identical spherical bodies is regularly packed within the chamber.

9. The fluid flow sensing device as claimed in claim 1, wherein said plurality of substantially identical spherical bodies is irregularly packed within the chamber.

10. The fluid flow sensing device as claimed in claim 1, wherein said plurality of substantially identical spherical bodies is so packed as to provide a close packing arrangement.

11. The fluid flow sensing device as claimed in claim 1, wherein the means to direct a flow of fluid through the chamber comprises a fluid inlet operatively connected to said first opening and a fluid outlet operatively connected to said second opening.

12. The fluid flow sensing device as claimed in claim 11, wherein the means to determine a differential pressure is operatively connected between said fluid inlet and said fluid outlet.

13. The fluid flow sensing device as claimed in claim 1, wherein each of said first opening and said second opening is provided with means to retain the plurality of substantially identical spherical bodies within the chamber.

14. The fluid flow sensing device as claimed in claim 1, wherein an average diameter of each of said plurality of substantially identical spherical bodies is between one third and one twentieth of a diameter of the chamber, said diameter of the chamber being a diameter taken orthogonally to a longitudinal axis of the chamber, said longitudinal axis of the chamber extending between said first opening and said second opening of the chamber.

15. The fluid flow sensing device as claimed in claim 14, wherein an average diameter of each of said plurality of substantially identical spherical bodies is between a quarter and a tenth of said diameter of the chamber.

16. The fluid flow sensing device as claimed in claim 1, wherein the fluid flow sensing device is so configured that said plurality of substantially identical spherical bodies may be removed from the chamber and replaced with a second plurality of substantially identical second bodies.

17. The fluid flow sensing device as claimed in claim 1, wherein the fluid comprises a gas and the fluid flow sensing device comprises a gas flow sensing device.

18. The fluid flow sensing device as claimed in claim 1, operatively connected to anesthetic ventilator apparatus.

19. The fluid flow sensing device as claimed in claim 1, wherein said plurality of substantially identical spherical bodies fill said chamber such that there is no direct unobstructed fluid passage extending straight between the first opening and the second opening.

* * * * *